(12) United States Patent
Suko

(10) Patent No.: US 11,788,068 B2
(45) Date of Patent: Oct. 17, 2023

(54) MODIFIED/MUTANT BACTERIAL LUCIFERASES

(71) Applicant: Roche Molecular Systems, Inc., Pleasanton, CA (US)

(72) Inventor: Shawn Lee Suko, Walnut Creek, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 116 days.

(21) Appl. No.: 16/758,372

(22) PCT Filed: Oct. 25, 2018

(86) PCT No.: PCT/EP2018/079234
§ 371 (c)(1),
(2) Date: Apr. 22, 2020

(87) PCT Pub. No.: WO2019/081620
PCT Pub. Date: May 2, 2019

(65) Prior Publication Data
US 2020/0339964 A1 Oct. 29, 2020

Related U.S. Application Data

(60) Provisional application No. 62/576,814, filed on Oct. 25, 2017.

(51) Int. Cl.
*C12N 9/02* (2006.01)
(52) U.S. Cl.
CPC .......... *C12N 9/0069* (2013.01); *C12N 9/0071* (2013.01); *C12Y 114/14003* (2013.01)
(58) Field of Classification Search
CPC .................................................. C12N 9/0069
See application file for complete search history.

(56) References Cited

U.S. PATENT DOCUMENTS

| | | | |
|---|---|---|---|
| 8,557,970 | B2 | 10/2013 | Encell et al. |
| 8,669,087 | B1 | 3/2014 | Squirrell et al. |
| 9,732,373 | B2 | 8/2017 | Encell et al. |
| 2012/0034672 | A1 | 2/2012 | Kim et al. |
| 2017/0204379 | A1 | 7/2017 | Ogo |

FOREIGN PATENT DOCUMENTS

| | | | |
|---|---|---|---|
| CN | 102459579 | A | 5/2012 |
| CN | 103160528 | A | 6/2013 |
| CN | 104178463 | * | 12/2014 |
| JP | H07222590 | A | 8/1995 |
| JP | 2009207447 | A | 9/2009 |
| JP | 2016082975 | A | 5/2016 |
| WO | 2007/064437 | A2 | 6/2007 |
| WO | 2010/119721 | A1 | 10/2010 |
| WO | 2013/052915 | A2 | 4/2013 |

OTHER PUBLICATIONS

Cui. Engineering an Enhanced, Thermostable, Monomeric Bacterial Luciferase Gene as a Reporter in Plant Protoplasts. Plos ONE. vol. 9, Issue 10, pp. 1-11. Oct. 2014.*
Q9S3Z1_ALIFS. UnitProtKB/TrEMBL Database. Oct. 5, 2016.*
Studer. Residue mutations and their impact on protein structure and function: detecting beneficial and pathogenic changes. Biochem. J. (2013) 449, 581-594.*
English Translation of CN 104178463. Retrieved on Aug. 8, 2022.*
Q9S3Z1_ALIFS. UniProtKB/TrEMBL. Oct. 5, 2016.*
Meighen, "Molecular Biology of Bacterial Bioluminescence," Microbiological Reviews 55(1):123-142 (1991).
O'Kane and Prasher, "MicroReview: Evolutionary origins of bacterial bioluminescence," Molecular Microbiology 6(4):443-449 (1992).
Thorne, et al., "Illuminating insights into firefly luciferase and other bioluminescent reporters used in chemical biology," Chem. Biol. 17(6):646-657 (2010).
Tong, et al., "Evidence for light perception in a bioluminescent organ," PNAS 106(24):9836-9841 (2009).
Urbanczyk, et al., "Reclassification of Vibrio fischeri, Vibrio logei, Vibrio salmonicida and Vibrio wodanis as Aliivibrio fischeri gen. nov., comb, nov., Aliivibrio logei comb, nov., Aliivibrio salmonicida comb. nov. and Aliivibrio wodanis comb, nov.," International Journal of Systematic and Evolutionary Microbiology 57:2823-2829 (2007).
International Searching Authority, Invitation to Pay Additional Fees and, Where Applicable, Protest Fee, for International Patent Application No. PCT/EP2018/079234 dated Jan. 2, 2019.
International Searching Authority, Notification of Transmittal of the International Search Report and the Written Opinion of the International Searching Authority, or the Declaration, for International Patent Application No. PCT/EP2018/079234 dated Feb. 26, 2019.
NCBI/NIH website, LLM Class Flavin-Dependent Oxidoreductase amino acid sequence (from Candidatus Enterovibrio luxaltus) Database Accession No. WP_096619747 (Oct. 9, 2017).
International Bureau, Notification Concerning Transmittal of International Preliminary Report on Patentability (Chapter I of the Patent Cooperation Treaty), for International Patent Application No. PCT/EP2018/079234 dated May 7, 2020.
Foran, D.R., et al., Nucleotide sequence of the LuxA and LuxB genes of the bioluminescent marine bacterium Vibrio fischeni, Nucleic Acids Research, 1988, p. 777, vol. 16, No. 2.

* cited by examiner

*Primary Examiner* — Yong D Pak
(74) *Attorney, Agent, or Firm* — Daniel E Agnew; Eric Grant Lee

(57) ABSTRACT

Modified or mutant bacterial luciferases having improved activity, as compared to wild type or unmodified bacterial luciferases, are described. The modified or mutant bacterial luciferases display increased light production and/or slower signal decay. Employing these modified or mutant bacterial luciferases improve a luminescence reporter system assay by increasing the detection sensitivity, resulting in improved bioreporter/reporter assays. The invention further provides methods for using the modified or mutant bacterial luciferases, reporter assays using the modified or mutant bacterial luciferases, and kits and articles of manufacture.

5 Claims, 7 Drawing Sheets

Specification includes a Sequence Listing.

SEQUENCE LISTING

<160> NUMBER OF SEQ ID NOS: 3

<210> SEQ ID NO 1
<211> LENGTH: 2092
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: E. coli codon-optimized wild type LuxAB
      (Aliivibrio fischeri)

<400> SEQUENCE: 1

```
atgaaatttg gtaacatctg cttctcgtac caaccgcctg gcgaaactca caaacaagtg        60
atggaccgtt tcgttcgcct gggtattgcg agcgaagagg tcggcttcga cacctactgg       120
accttggagc atcattttac cgagtttggt ttgaccggca acctgtttgt ggcggcagca       180
aatctgttgg gtcgtaccaa gacgctgaat gttggcacca tgggcgttgt gattccgacg       240
gcacacccgg tgcgccagct ggaagatgtg ctgctgctgg atcagatgtc caagggccgc       300
ttcaacttcg gtaccgtgcg cggtctgtac cacaaagatt tccgtgtttt tggcgtcgac       360
atggaagaga gccgtgccat tacgcaaaac ttttatcaaa tgattatgga aagcctgcag       420
accggtacca tcagcagcga ttctgattac attcagtttc cgaaagtcga cgtctatcca       480
aaggtttatt ccaaaaacgt tccgacgtgt atgaccgcag agtctgcgag cacgacggaa       540
tggctggcta ttcagggtct gccgatggtc ttatcctgga ttatcggtac gaatgagaaa       600
aaagcgcaaa tggaattgta caacgagatt gccaccgagt atggccatga catcagcaag       660
atcgaccact gtatgaccta tatctgcagc gttgacgatg acgcgcaaaa ggctcaagac       720
gtttgccgtg agtttctgaa gaactggtat gattcttacg tgaatgcgac gaacattttc       780
aatgatagca atcagacccg tggttacgac taccacaagg tcagtggcg cgatttcgtt       840 ctgcagggtc atacgaatac taatcgtcgt gtcgattaca gcaacggtat taacccgta       900 ggcaccccgg agcaatgcat cgagatcatc cagcgtgaca tcgacgctac cggtatcacg       960
aatatcacgt gtggttttga ggcgaacggt actgaagatg aaatcatcgc cagcatgcgt      1020
cgcttcatga cccaagtggc gccgttcctg aaagaaccga gtgaggatc cctaggaata      1080
```

-continued

```
attttgttta actttaagaa ggagataaaa aatgaaattt ggtctgtttt tcctgaattt    1140
tcaaaaggat ggcatcacga gcgaagaaac cctggacaac atggtcaaga ctgttacgtt    1200
gattgatagc accaagtatc acttcaatac ggcctttgtt aacgaacacc actttagcaa    1260
aaacggtatt gtgggcgcac cgattaccgc ggctggtttt ctgctgggtc tgaccaacaa    1320
gctccacatc ggctcgctga accaagtcat caccacccac cacccggttc gtgtcgcaga    1380
agaggcgagc ctgttggacc agatgtctga gggtcgtttc attctgggtt tcagcgattg    1440
tgagagcgac ttcgagatgg aattttttccg tcgtcatatc agcagccgtc aacaacagtt    1500
tgaggcatgc tatgaaatca ttaatgacgc cctgaccacc ggctactgtc atccgcagaa    1560
tgatttctac gatttcccta aggttagcat taacccgcat tgctattccg agaatggccc    1620
aaagcaatat gtgagcgcaa ccagcaaaga agtcgtgatg tgggctgcga agaaagcgct    1680
gccgctgacg ttcaaatggg aagataacct ggaaacgaaa gagcgctacg cgatcctgta    1740
taacaagacc gcgcagcagt acggtatcga catctctgac gtggaccacc agttgaccgt    1800
tattgcgaat ctgaatgccg atcgcagcac ggcgcaggaa gaggttcgcg agtacctgaa    1860
agattacatt acggaaacct acccgcagat ggaccgtgac gagaaaatca actgcatcat    1920
tgaagagaac gcagtgggct cccatgacga ctactatgag agcactaaac tggccgtcga    1980
gaaaaccggt tccaagaaca ttctgttgag cttcgagagc atgagcgata tcaaagatgt    2040
gaaagacatt atcgacatgc tgaatcaaaa gattgagatg aatctgccgt ga          2092
```

<210> SEQ ID NO 2
<211> LENGTH: 354
<212> TYPE: PRT
<213> ORGANISM: Aliivibrio fischeri
<220> FEATURE:
<223> OTHER INFORMATION: LuxA

<400> SEQUENCE: 2

```
Met Lys Phe Gly Asn Ile Cys Phe Ser Tyr Gln Pro Pro Gly Glu Thr
1               5                   10                  15

His Lys Gln Val Met Asp Arg Phe Val Arg Leu Gly Ile Ala Ser Glu
            20                  25                  30

Glu Val Gly Phe Asp Thr Tyr Trp Thr Leu Glu His His Phe Thr Glu
        35                  40                  45

Phe Gly Leu Thr Gly Asn Leu Phe Val Ala Ala Ala Asn Leu Leu Gly
    50                  55                  60

Arg Thr Lys Thr Leu Asn Val Gly Thr Met Gly Val Val Ile Pro Thr
65                  70                  75                  80

Ala His Pro Val Arg Gln Leu Glu Asp Val Leu Leu Leu Asp Gln Met
                85                  90                  95

Ser Lys Gly Arg Phe Asn Phe Gly Thr Val Arg Gly Leu Tyr His Lys
            100                 105                 110

Asp Phe Arg Val Phe Gly Val Asp Met Glu Glu Ser Arg Ala Ile Thr
        115                 120                 125

Gln Asn Phe Tyr Gln Met Ile Met Glu Ser Leu Gln Thr Gly Thr Ile
    130                 135                 140

Ser Ser Asp Ser Asp Tyr Ile Gln Phe Pro Lys Val Asp Val Tyr Pro
145                 150                 155                 160

Lys Val Tyr Ser Lys Asn Val Pro Thr Cys Met Thr Ala Glu Ser Ala
                165                 170                 175

Ser Thr Thr Glu Trp Leu Ala Ile Gln Gly Leu Pro Met Val Leu Ser
            180                 185                 190
```

```
Trp Ile Ile Gly Thr Asn Glu Lys Lys Ala Gln Met Glu Leu Tyr Asn
            195                 200                 205

Glu Ile Ala Thr Glu Tyr Gly His Asp Ile Ser Lys Ile Asp His Cys
210                 215                 220

Met Thr Tyr Ile Cys Ser Val Asp Asp Ala Gln Lys Ala Gln Asp
225                 230                 235                 240

Val Cys Arg Glu Phe Leu Lys Asn Trp Tyr Asp Ser Tyr Val Asn Ala
                245                 250                 255

Thr Asn Ile Phe Asn Asp Ser Asn Gln Thr Arg Gly Tyr Asp Tyr His
            260                 265                 270

Lys Gly Gln Trp Arg Asp Phe Val Leu Gln Gly His Thr Asn Thr Asn
                275                 280                 285

Arg Arg Val Asp Tyr Ser Asn Gly Ile Asn Pro Val Gly Thr Pro Glu
            290                 295                 300

Gln Cys Ile Glu Ile Ile Gln Arg Asp Ile Asp Ala Thr Gly Ile Thr
305                 310                 315                 320

Asn Ile Thr Cys Gly Phe Glu Ala Asn Gly Thr Glu Asp Glu Ile Ile
                325                 330                 335

Ala Ser Met Arg Arg Phe Met Thr Gln Val Ala Pro Phe Leu Lys Glu
            340                 345                 350

Pro Lys

<210> SEQ ID NO 3
<211> LENGTH: 326
<212> TYPE: PRT
<213> ORGANISM: Aliivibrio fischeri
<220> FEATURE:
<223> OTHER INFORMATION: LuxB

<400> SEQUENCE: 3

Met Lys Phe Gly Leu Phe Phe Leu Asn Phe Gln Lys Asp Gly Ile Thr
1               5                   10                  15

Ser Glu Glu Thr Leu Asp Asn Met Val Lys Thr Val Thr Leu Ile Asp
                20                  25                  30

Ser Thr Lys Tyr His Phe Asn Thr Ala Phe Val Asn Glu His His Phe
            35                  40                  45

Ser Lys Asn Gly Ile Val Gly Ala Pro Ile Thr Ala Ala Gly Phe Leu
        50                  55                  60

Leu Gly Leu Thr Asn Lys Leu His Ile Gly Ser Leu Asn Gln Val Ile
65                  70                  75                  80

Thr Thr His His Pro Val Arg Val Ala Glu Glu Ala Ser Leu Leu Asp
                85                  90                  95

Gln Met Ser Glu Gly Arg Phe Ile Leu Gly Phe Ser Asp Cys Glu Ser
            100                 105                 110

Asp Phe Glu Met Glu Phe Phe Arg Arg His Ile Ser Ser Arg Gln Gln
        115                 120                 125

Gln Phe Glu Ala Cys Tyr Glu Ile Ile Asn Asp Ala Leu Thr Thr Gly
    130                 135                 140

Tyr Cys His Pro Gln Asn Asp Phe Tyr Asp Phe Pro Lys Val Ser Ile
145                 150                 155                 160

Asn Pro His Cys Tyr Ser Glu Asn Gly Pro Lys Gln Tyr Val Ser Ala
                165                 170                 175

Thr Ser Lys Glu Val Val Met Trp Ala Ala Lys Ala Leu Pro Leu
            180                 185                 190
```

-continued

```
Thr Phe Lys Trp Glu Asp Asn Leu Glu Thr Lys Glu Arg Tyr Ala Ile
        195                 200                 205

Leu Tyr Asn Lys Thr Ala Gln Gln Tyr Gly Ile Asp Ile Ser Asp Val
    210                 215                 220

Asp His Gln Leu Thr Val Ile Ala Asn Leu Asn Ala Asp Arg Ser Thr
225                 230                 235                 240

Ala Gln Glu Glu Val Arg Glu Tyr Leu Lys Asp Tyr Ile Thr Glu Thr
                245                 250                 255

Tyr Pro Gln Met Asp Arg Asp Glu Lys Ile Asn Cys Ile Ile Glu Glu
            260                 265                 270

Asn Ala Val Gly Ser His Asp Asp Tyr Tyr Glu Ser Thr Lys Leu Ala
        275                 280                 285

Val Glu Lys Thr Gly Ser Lys Asn Ile Leu Leu Ser Phe Glu Ser Met
    290                 295                 300

Ser Asp Ile Lys Asp Val Lys Asp Ile Ile Asp Met Leu Asn Gln Lys
305                 310                 315                 320

Ile Glu Met Asn Leu Pro
                325
```

US 11,788,068 B2

MODIFIED/MUTANT BACTERIAL LUCIFERASES

CROSS REFERENCE TO RELATED APPLICATIONS

This present patent application is the U.S. national stage entry of International Patent Application PCT/EP2018/079234, filed Oct. 25, 2018, which claims priority to U.S. Provisional Patent Application No. 62/576,814, filed Oct. 25, 2017, the disclosures of which are incorporated herein by reference in their entireties.

SEQUENCE LISTING

The instant application contains a Sequence Listing, which has been submitted electronically in ASCII format and is hereby incorporated by reference in its entirety. Said ASCII copy, created on Apr. 28, 2020, is named P34374-US1_SL.txt and is 9,279 bytes in size.

FIELD OF THE INVENTION

The present disclosure relates broadly to the field bioreporter/reporter assays. Within, this field, the present invention is directed to improved luminescence reporter system assays. In particular, the present invention concerns improved modified bacterial luciferases that display increased light production and/or slower signal decay, compared to wild type or parental enzymes. Employing these improved modified bacterial luciferases would improve a luminescence reporter system assay by increasing its detection sensitivity. The improved modified bacterial luciferases, therefore, allows for a more efficient and sensitive bioreporter/reporter assay. The invention further provides methods for using modified bacterial luciferases, and reporter assays using modified bacterial luciferases.

BACKGROUND OF THE INVENTION

In the field of bioreporter/reporter assays, the use of bioluminescence is of considerable significance and importance. Bioluminescence, a form of chemiluminscence, is the production and emission of light by a living organism. The principal chemical reaction in bioluminescence involves the light-emitting pigment luciferin substrate and the enzyme luciferase. The enzyme, luciferase, catalyzes the oxidation of luciferin substrate. Although all luciferases catalyze light-emitting reactions, the luciferin substrates are structurally diverse (see, Thorne, et al., Chem. Biol. 17(6):646-657 (2010)). Bioluminescence has widespread applications in both biology and medicine. In particular, bioluminescent organisms are a target for many areas of research. Luciferase systems are widely used in genetic engineering as reporter genes, each producing a different color by fluorescence, and for biomedical research using bioluminescence imaging. Examples of such applications include use of the firefly luciferase gene for studying transgenic tobacco plants, bioluminescent activated destruction experimental cancer treatment, and optogenetics. Thus, bioluminescence is a commonly exploited detection technology used across academia and industry. In fact, of the nearly 2,000 assays listed in the PubChem database in 2010, approximately 21% are bioluminescence and 53% are fluorescence (see, Thorne, et al., Chem. Biol. 17(6):646-657 (2010)).

Luciferase is a class of oxidative enzymes that produce bioluminescence. One example is the firefly luciferase (EC 1.13.12.7) from the firefly *Photinus pyralis*. "Firefly luciferase" as a laboratory reagent often refers to *P. pyralis* luciferase, although recombinant luciferases from several other species of fireflies are also commercially available. Bacterial bioluminescence is seen in *Photobacterium* species, which include *Aliivibrio fischeri* (previously known as *Vibrio fischeri*), *Vibrio haweyi*, and *Vibrio harveyi*. It is noted that recently, a new genus, *Aliivibrio* gen. nov., was established in order to accommodate *Vibrio fischeri*, *Vibrio logei*, *Vibrio salmonicada*, and *Vibrio wodanis*, which are now known as *Aliivibrio fischeri* comb. nov. (the type species), *Aliivibrio* logei comb. nov., *Aliivibrio salmonicida* comb. nov., and *Aliivibrio wodanis* comb. nov., respectively (see, Urbanczyk, et al., International Journal of Systematic and Evolutionary Microbiology 57:2823-2829 (2007)). In particular, *Aliivibrio fischeri* is a gram-negative, rod-shaped bacterium found globally in marine environments. The bacterial luciferin-luciferase system is encoded by a set of genes labelled the Lux operon. The Lux operon is a 9-kilobase fragment of the *A. fischeri* genome that controls bioluminescence through the catalyzation of the enzyme luciferase. The operon has a known sequence of luxCDAB(F)E, where luxA and luxB encode the components of luciferase. Bacterial luciferase is a hterodimeric enzyme of 77 kDa composed of α and β subunits with molecular masses of 40 and 37 kDa, respectively (Meighen, Microbiological Reviews 55:123-142 (1991)). The two α and β subunits encoded on closely linked adjacent genes, luxA and luxB in the lux operon, likely arose from gene duplication, because there is about 30% identity in the amino acid sequence between the α and β subunits of all bacterial luciferases (Meighen (1991)). The light-emitting reaction in bacteria involves the enzymatic oxidation of two simple substrates: (1) a long-chain aliphatic aldehyde (RCHO) and a reduced flavin mononucleotide ($FMNH_2$). With luciferase, the excess free energy is liberated as light (O'Kane and Prasher, Molecular Microbiology 6(4):443-449 (1992)). The aldehyde is consumed during the reaction but is continuously synthesized by the bacteria, resulting in a persistent glow (Widder, Science 328:5979:704-708 (2010)).

Thus, there is always a need in the art for improvements on existing compositions and methods. For example, there is a need in the art to provide improved luciferases. There is, in particular, a need for improved bacterial luciferases, in order to increase the sensitivity of methods and assays that employ luciferases.

SUMMARY OF THE INVENTION

Provided herein are modified luciferases having improved activities, including increased light production, and/or slower/decreased signal decay, relative to wild type or control luciferases. Because luciferase-based luminescence reporter system assays are commonly used in biology and medicine, such modified luciferases with improved activities might then increase the sensitivity of luminescence reporter system assays.

Certain embodiments in the present disclosure relate to new compositions of and methods of using modified improved bacterial luciferases. Luciferases are used in numerous and various luminescence reporter system assays. In some embodiments, the improved modified bacterial luciferase has increased efficiency and/or activity as compared with a control/wild type bacterial luciferase.

Embodiments of the present disclosure provide for a modified bacterial luciferase having improved activity as compared to a control bacterial luciferase, wherein the LuxA subunit of the modified bacterial luciferase comprises an amino acid sequence that is at least 80% identical to the LuxA subunit of the control bacterial luciferase, wherein the LuxA subunit of the control bacterial luciferase has an amino acid sequence of SEQ ID NO:2. In a related embodiment, the improved activity is an increase in light production and/or slower signal decay, as compared to the control bacterial luciferase. In another embodiment, (a) the amino acid of the modified bacterial luciferase corresponding to position 170 of SEQ ID NO:2 is R, W, or K; (b) the amino acid of the modified bacterial luciferase corresponding to position 102 of SEQ ID NO:2 is K; (c) the amino acid of the modified bacterial luciferase corresponding to position 264 of SEQ ID NO:2 is D; (d) the amino acid of the modified bacterial luciferase corresponding to position 286 of SEQ ID NO:2 is D; (e) the amino acid of the modified bacterial luciferase corresponding to position 22 of SEQ ID NO:2 is H; or (f) the amino acid of the modified bacterial luciferase corresponding to position 166 of SEQ ID NO:2 is Y. In a related embodiment, the amino acid of the modified bacterial luciferase corresponding to position 170 of SEQ ID NO:2 is R. In another embodiment, (a) the amino acid of the modified bacterial luciferase corresponding to position 168 of SEQ ID NO:2 is R, and the amino acid of the modified bacterial luciferase corresponding to position 309 of SEQ ID NO:2 is T; (b) the amino acid of the modified bacterial luciferase corresponding to position 218 of SEQ ID NO:2 is V, and the amino acid of the modified bacterial luciferase corresponding to position 224 of SEQ ID NO:2 is R; (c) the amino acid of the modified bacterial luciferase corresponding to position 172 of SEQ ID NO:2 is I, and the amino acid of the modified bacterial luciferase corresponding to position 236 of SEQ ID NO:2 is R; (d) the amino acid of the modified bacterial luciferase corresponding to position 286 of SEQ ID NO:2 is D, and the amino acid of the modified bacterial luciferase corresponding to position 308 of SEQ ID NO:2 is D; (e) the amino acid of the modified bacterial luciferase corresponding to position 11 of SEQ ID NO:2 is L, and the amino acid of the modified bacterial luciferase corresponding to position 261 of SEQ ID NO:2 is D; or (f) the amino acid of the modified bacterial luciferase corresponding to position 130 of SEQ ID NO:2 is I, and the amino acid of the modified bacterial luciferase corresponding to position 224 of SEQ ID NO:2 is R. Embodiments of the present disclosure provide for a recombinant nucleic acid encoding the modified bacterial luciferase of the invention. Embodiments of the present disclosure also provide for an expression vector comprising the recombinant nucleic acid encoding the modified bacterial luciferases of the invention. Further embodiments of the present disclosure provide for a host cell comprising the expression vector comprising the recombinant nucleic acid encoding the modified bacterial luciferases of the invention.

Embodiments of the present disclosure also provide for a modified bacterial luciferase having improved activity as compared to a control bacterial luciferase, wherein the LuxA subunit of the modified bacterial luciferase comprises an amino acid sequence that is at least 80% identical to the LuxA subunit of the control bacterial luciferase, wherein the LuxA subunit of the control bacterial luciferase has an amino acid sequence of SEQ ID NO:2, and comprises at least one amino acid substitution at position corresponding to position 11, 22, 102, 130, 166, 168, 170, 172, 218, 224, 236, 261, 264, 286, 308, or 309 of SEQ ID NO:2. In a related embodiment, the improved activity is an increase in light production and/or slower signal decay, as compared to the control bacterial luciferase. In another embodiment, (a) the amino acid of the modified bacterial luciferase corresponding to position 170 of SEQ ID NO:2 is R, W, or K; or (b) the amino acid of the modified bacterial luciferase corresponding to position 102 of SEQ ID NO:2 is K; (c) the amino acid of the modified bacterial luciferase corresponding to position 264 of SEQ ID NO:2 is D; (d) the amino acid of the modified bacterial luciferase corresponding to position 286 of SEQ ID NO:2 is D; (e) the amino acid of the modified bacterial luciferase corresponding to position 22 of SEQ ID NO:2 is H; or (f) the amino acid of the modified bacterial luciferase corresponding to position 166 of SEQ ID NO:2 is Y. In a related embodiment, the amino acid of the modified bacterial luciferase corresponding to position 170 of SEQ ID NO:2 is R. In one embodiment, (a) the amino acid of the modified bacterial luciferase corresponding to position 168 of SEQ ID NO:2 is R, and the amino acid of the modified bacterial luciferase corresponding to position 309 of SEQ ID NO:2 is T; (b) the amino acid of the modified bacterial luciferase corresponding to position 218 of SEQ ID NO:2 is V, and the amino acid of the modified bacterial luciferase corresponding to position 224 of SEQ ID NO:2 is R; (c) the amino acid of the modified bacterial luciferase corresponding to position 172 of SEQ ID NO:2 is I, and the amino acid of the modified bacterial luciferase corresponding to position 236 of SEQ ID NO:2 is R; (d) the amino acid of the modified bacterial luciferase corresponding to position 286 of SEQ ID NO:2 is D, and the amino acid of the modified bacterial luciferase corresponding to position 308 of SEQ ID NO:2 is D; (e) the amino acid of the modified bacterial luciferase corresponding to position 11 of SEQ ID NO:2 is L, and the amino acid of the modified bacterial luciferase corresponding to position 261 of SEQ ID NO:2 is D; or (f) the amino acid of the modified bacterial luciferase corresponding to position 130 of SEQ ID NO:2 is I, and the amino acid of the modified bacterial luciferase corresponding to position 224 of SEQ ID NO:2 is R. Embodiments of the present disclosure also provide for a recombinant nucleic acid encoding the modified bacterial luciferase of the invention. Embodiments of the present disclosure also provide for an expression vector comprising the recombinant nucleic acid of encoding the modified bacterial luciferases of the invention. Other embodiments of the present disclosure also provide for a host cell comprising the expression vector comprising the recombinant nucleic acids encoding the modified bacterial luciferases of the invention.

Embodiments of the present disclosure also provide for a recombinant nucleic acid encoding a modified bacterial luciferase having improved activity as compared to a control bacterial luciferase, wherein the LuxA subunit of the modified bacterial luciferase comprises an amino acid sequence that is at least 80% identical to the LuxA subunit of the control bacterial luciferase, wherein the LuxA subunit of the control bacterial luciferase has an amino acid sequence of SEQ ID NO:2. In a related embodiment, the improved activity is an increase in light production and/or slower signal decay, as compared to the control bacterial luciferase. In another embodiment, (a) the amino acid of the modified bacterial luciferase corresponding to position 170 of SEQ ID NO:2 is R, W, or K; (b) the amino acid of the modified bacterial luciferase corresponding to position 102 of SEQ ID NO:2 is K; (c) the amino acid of the modified bacterial luciferase corresponding to position 264 of SEQ ID NO:2 is D; (d) the amino acid of the modified bacterial luciferase corresponding to position 286 of SEQ ID NO:2 is D; (e) the amino acid of the modified bacterial luciferase corresponding to position 22 of SEQ ID NO:2 is H; or (f) the amino acid of the modified bacterial luciferase corresponding to position 166 of SEQ ID NO:2 is Y. In a related embodiment, the amino acid of the modified bacterial luciferase corresponding to position 170 of SEQ ID NO:2 is R. In another embodiment, the nucleic acid sequence encoding the LuxA subunit is at least 80% identical to SEQ ID NO:1. Embodiments of the present disclosure also provide for a recombinant nucleic acid encoding a modified bacterial luciferase of the invention. Embodiments of the present disclosure provide for an expression vector comprising the recombinant nucleic acid encoding a modified bacterial luciferase of the invention. Embodiments of the present disclosure also provide for a host cell comprising the expression vector comprising the recombinant nucleic acid encoding a modified bacterial luciferase of the invention. In another embodiment, (a) the amino acid of the modified bacterial luciferase corresponding to position 168 of SEQ ID NO:2 is R, and the amino acid of the modified bacterial luciferase corresponding to position 309 of SEQ ID NO:2 is T; (b) the amino acid of the modified bacterial luciferase corresponding to position 218 of SEQ ID NO:2 is V, and the amino acid of the modified bacterial luciferase corresponding to position 224 of SEQ ID NO:2 is R; (c) the amino acid of the modified bacterial luciferase corresponding to position 172 of SEQ ID NO:2 is I, and the amino acid of the modified bacterial luciferase corresponding to position 236 of SEQ ID NO:2 is R; (d) the amino acid of the modified bacterial luciferase corresponding to position 286 of SEQ ID NO:2 is D, and the amino acid of the modified bacterial luciferase corresponding to position 308 of SEQ ID NO:2 is D; (e) the amino acid of the modified bacterial luciferase corresponding to position 11 of SEQ ID NO:2 is L, and the amino acid of the modified bacterial luciferase corresponding to position 261 of SEQ ID NO:2 is D; or (f) the amino acid of the modified bacterial luciferase corresponding to position 130 of SEQ ID NO:2 is I, and the amino acid of the modified bacterial luciferase corresponding to position 224 of SEQ ID NO:2 is R. In a related embodiment, the nucleic acid sequence encoding the LuxA subunit is at least 80% identical to SEQ ID NO:1. Embodiments of the present disclosure also provide for an expression vector comprising the recombinant nucleic acid of encoding a modified bacterial luciferase of the invention. Embodiments of the present disclosure also provide for a host cell comprising the expression vector comprising the recombinant nucleic acid of encoding a modified bacterial luciferase of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 4A shows crude lysates run on a stain-free polyacrylamide gel, revealing two distinct bands corresponding to both α- and β-subunits. The standard curve generated is depicted in FIG. 4B.

DETAILED DESCRIPTION OF THE INVENTION

Figure 1:
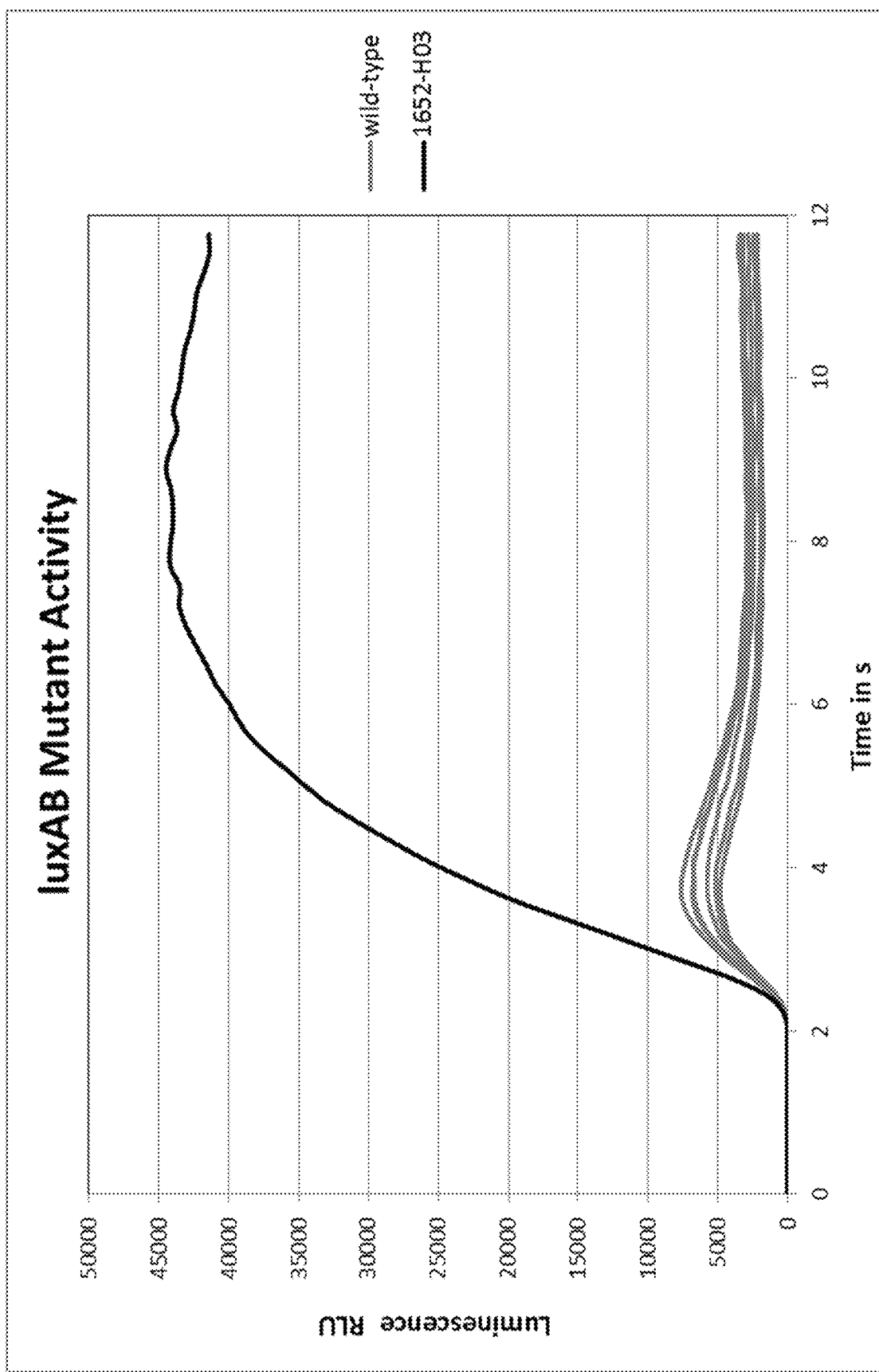
FIG. 1 shows luminescence activity of candidate modified bacterial luciferase clone 1652 H03 (with a C170R mutation), as compared to wild type bacterial luciferase.

The present invention relates to modified bacterial luciferases that exhibit improved activity, as compared to wild type or unmodified bacterial luciferases. Traditional luciferase enzymes, including bacterial or from other sources, are widely employed in the field of bioreporter/reporter assays. Bioluminescence involves the oxidation of a substrate, such as luciferin, by the enzyme luciferase. Just as there are a number of different luciferase enzymes, from a number of different organisms, the luciferin substrate is also very diverse. The modified bacterial luciferases of the present invention display increased light production and/or exhibit slower rate decay, as compared to wild type or unmodified bacterial luciferases. These modified bacterial luciferases may be employed in luminescence reporter system assays that are widely used in biology and medicine, as well as other disciplines, where light-based reporting is employed, particularly one based on luciferin substrate.

Use of modified bacterial luciferases that are an improvement over wild type or unmodified bacterial luciferases, will allow for increased sensitivity in bioreporter/reporter assays that use bioluminescence reporters. Increased sensitivity, in turn, allows for a more robust reporter assay that can detect even small amounts or trace amounts of whatever the target is.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002), which is incorporated by reference. Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466, which are both incorporated by reference). The term "amino acid" also includes unnatural amino acids, modified amino acids (e.g., having modified side chains and/or backbones), and amino acid analogs (see, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "luminescence" refers to the light output of the luciferase enzyme/polypeptide under certain given conditions. Luminescence may be measured as an instantaneous or near-instantaneous measure of light output shortly after the start of the luminescence reaction, which is known as "flash." Additionally, luminescence may be measured over a period of time, for example, in the same reaction for a period of seconds, minutes, hours, etc. Luminescence may be reported in a number of different formats, including as the average over a given time, the half-life of decay of signal, the sum of the signal over a period of time, or as the peak output. The terms "bioluminescence" or "luminescence" can also generally refer to light produced as a result of a reaction between an enzyme and a substrate that generates light.

The term "biological sample" encompasses a variety of sample types obtained from an organism and can be used in a diagnostic or monitoring assay. The term encompasses urine, urine sediment, blood, saliva, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, biological fluids, and tissue samples.

The term "mutant" or "modified," in the context of luciferases of the present invention, means a polypeptide, typically recombinant, that comprises one or more amino acid substitutions relative to a corresponding, functional luciferases, such as a bacterial luciferase.

In the context of mutant luciferase or modified luciferase, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. An amino acid "corresponding to position [X] of [specific sequence]" refers to an amino acid in a polypeptide of interest that aligns with the equivalent amino acid of a specified sequence. Generally, as described herein, the amino acid corresponding to a position of a luciferase can be determined using an alignment algorithm such as BLAST as described below. Because not all positions within a given "corresponding region" need be identical, non-matching positions within a corresponding region may be regarded as "corresponding positions." Accordingly, as used herein, referral to an "amino acid position corresponding to amino acid position [α]" of a specified luciferase refers to equivalent positions, based on alignment, in other luciferase and structural homologues and families. In some embodiments of the present invention, "correspondence" of amino acid positions are determined with respect to a region of the luciferase comprising one or more motifs of luxA (SEQ ID NO:2) or luxB (SEQ ID NO3). When a luciferase polypeptide sequence differs from SEQ ID NOs:2 or 3 (e.g., by changes in amino acids or addition or deletion of amino acids), it may be that a particular mutation or modification associated with improved activity as discussed herein will not be in the same position number as it is in SEQ ID NOs:2 or 3.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by restriction endonucleases, in a form not normally found in nature. Thus an isolated, mutant or modified luciferase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" or a "recombinant polypeptide" is a protein/polypeptide made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (Meth. Enzymol. 68:90-99, 1979); the phosphodiester method of Brown et al. (Meth. Enzymol. 68:109-151, 1979); the diethylphosphoramidite method of Beaucage et al. (Tetrahedron Lett. 22:1859-1862, 1981); the triester method of Matteucci et al. (J. Am. Chem. Soc. 103:3185-3191, 1981); automated synthesis methods; or the solid support method of U.S. Pat. No. 4,458,066, entitled "Process for Preparing Polynucleotides," issued Jul. 3, 1984 to Caruthers et al., or other methods known to those skilled in the art. All of these references are incorporated by reference.

The term "unmodified form," in the context of a mutant or modified luciferase, is a term used herein for purposes of defining a mutant or modified luciferase of the present invention: the term "unmodified form" refers to a functional luciferase that has the amino acid sequence of the mutant or modified luciferase except at one or more amino acid position(s) specified as characterizing the mutant or modified luciferase. Thus, reference to a mutant or modified luciferase in terms of (a) its unmodified form and (b) one or more specified amino acid substitutions means that, with the exception of the specified amino acid substitution(s), the mutant or modified luciferase otherwise has an amino acid sequence identical to the unmodified form in the specified motif. The "unmodified luciferase" (and therefore also the mutant or modified form having increased luciferase activity (i.e., increased light production and/or slower signal decay) may contain additional mutations to provide desired functionality. Accordingly, in carrying out the present invention as described herein, the unmodified form of a luciferase is predetermined. The unmodified form of a luciferase can be, for example, a wild-type and/or a naturally occurring luciferase, or a luciferase that has already been intentionally modified. An unmodified form of the luciferase is preferably a bacterial luciferase, as well as functional variants thereof having substantial sequence identity to a wild-type or naturally occurring luciferase.

The term "codon optimized," "codon-optimized," "codon-optimised," or "codon usage bias" refers to the practice of choosing codons (i.e., codon usage) in such a way as to optimize or tailor expression, as needed (i.e., a technique to improve the protein expression in living organisms by increasing the translation efficiency of a gene of interest). Said another way, codon optimization is a method of adjusting codons to match host tRNA abundances, and has traditionally been used for expression of a heterologous gene. New strategies for optimization of heterologous expression consider global nucleotide content such as local mRNA folding, codon pair bias, a codon ramp or codon correlations. Codon optimization is possible because the inherent in degeneracy of codons. Degeneracy results because there are more codons than encodable amino acids. Thus, the vast majority of amino acids are encoded by multiple codons, which means there are multiple tRNAs (with different anti-codon loops) that carry any given amino acid. As such, different codons may be used, without changing the amino acid sequence that is encoded. That is, a gene or section of nucleic acid may be mutated/altered (or synthesized de novo) to change the codons used for coding particular amino acids, without changing the amino acid sequence of the polypeptide/protein itself. For example, rare codons can be replaced with more abundant codons, while keeping the amino acid sequence unchanged. Optimal codons in fast-growing microorganisms, like *Escherichia coli* or *Saccharomyces cerevisiae* (baker's yeast), reflect the composition of their respective genomic tRNA pool. It is believed that optimal codons help to achieve faster translation rates and high accuracy. As a result of these factors, translational selection is expected to be stronger in highly-expressed genes. In other organisms that do not show high growing rates or that present small genomes, codon usage optimization is normally absent, and codon preferences are determined by the characteristic mutational biases seen in that particular genome. Several viral families (herpesvirus, lentivirus, papillomavirus, polyomavirus, adenovirus, and parvovirus) are known to encode structural proteins that display heavily-skewed codon usage compared to the host cell. The suggestion has been made that these codon biases play a role in the temporal regulation of their late proteins. In the present invention, the wild type or unmodified luxAB luciferase gene is *E. coli* codon-optimized wild type luxAB (*Aliivibrio fischeri*) (SEQ ID NO:1).

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 60%, at least 65%, at least 70%, at least 75%, at least 80%, at least 85%, at least 90%, or at least 95% identity over a specified region)), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are also "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Examples of an algorithm that is suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

The term "complement thereof" refers to nucleic acid that is both the same length as, and exactly complementary to, a given nucleic acid.

Also provided are recombinant nucleic acids encoding any of the luciferases of the present invention. Using a nucleic acid of the present invention, encoding a luciferase, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the luciferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the luciferases. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag." However, these are generally unnecessary when purifying a thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the luciferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., Molecular Cloning: A Laboratory Manual (Cold Spring Harbor Laboratory Press, New York, N.Y., 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a luciferase is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include CaPO4 precipitation, liposome fusion, LIPOFECTIN®, electroporation, viral infection, and the like.

In some embodiments, prokaryotes are typically used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in Genetic Engineering, Principles and Methods 12:275-296 (Plenum Publishing Corp., 1990); Hanahan et al., Meth. Enzymol., 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

The luciferases of the present invention may be produced by culturing a host cell transformed with an expression vector containing a nucleic acid encoding the luciferase, under the appropriate conditions to induce or cause expression of the luciferase. Methods of culturing transformed host cells under conditions suitable for protein expression are well-known in the art (see, e.g., Sambrook et al., supra). Suitable host cells for production of the luciferase from lambda pL promotor-containing plasmid vectors may include *E. coli* strain DG116 (ATCC No. 53606) (see U.S. Pat. No. 5,079,352 and Lawyer, F. C. et al., PCR Methods and Applications 2:275-87, 1993, which are both incorporated herein by reference). Following expression, the luciferase can be harvested and isolated.

The improved luciferases of the present invention may be used for any purpose in which such enzyme activity is necessary or desired. Accordingly, in another aspect of the invention, methods of using the modified/mutant bacterial luciferases, such as in a bioreporter/reporter assay system, wherein luminescence/bioluminescence is the relevant readout.

In some embodiments, the improved luciferase has improved activity, such as increased light production and/or slower signal decay. It was not previously appreciated that the substitutions at any one or more of the amino acid corresponding to position 11, 22, 102, 130, 166, 168, 170, 172, 218, 224, 236, 261, 264, 286, 308, 309, and/or 334 of the luxA subunit of *Aliivibrio fischeri* luciferase (SEQ ID NO:2) would result in increased activity. Thus, in some embodiments, single mutant/modification luciferases that have improved activity have: (a) a C to R substitution at position 170 of the luxA subunit (SEQ ID NO:2), (b) a N to K substitution at position 102 of the luxA subunit (SEQ ID NO:2), (c) a N to D substitution at position 264 of the luxA subunit (SEQ ID NO:2), (d) a N to D substitution at position 286 of the luxA subunit (SEQ ID NO:2), (e) a D to H substitution at position 22 of the luxA subunit (SEQ ID NO:2), (f) a N to Y substitution at position 166 of the luxA subunit (SEQ ID NO:2), (g) a C to W substitution at position 170 of the luxA subunit (SEQ ID NO:2), or (h) a C to K substitution at position 170 of the luxA subunit (SEQ ID NO:2). In some embodiments, the modified luciferase having improved activity has two mutations/modifications, such as: (a) a P to R substitution at position 168, and an I to T substitution at position 309 of the luxA subunit (SEQ ID NO:2), (b) an I to V substitution at position 218, and a C to R substitution at position 224 of the luxA subunit (SEQ ID NO:2), (c) a T to I substitution at position 172, and a Q to R substitution at position 236 of the luxA subunit (SEQ ID NO:2), (d) a N to D substitution at position 286, and an E to D substitution at position 308 of the luxA subunit (SEQ ID NO:2), (e) a Q to L substitution at position 11, and an N to D substitution at position 261 of the luxA subunit (SEQ ID NO:2), or (f) an N to I substitution at position 130, and an E to G substitution at position 334 of the luxA subunit (SEQ ID NO:2). In some embodiments, the luciferase having improved activity has at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to SEQ ID NOs:2, and comprises: (a) a C to R substitution at position 170 of the luxA subunit (SEQ ID NO:2), (b) a N to K substitution at position 102 of the luxA subunit (SEQ ID NO:2), (c) a N to D substitution at position 264 of the luxA subunit (SEQ ID NO:2), (d) a N to D substitution at position 286 of the luxA subunit (SEQ ID NO:2), (e) a D to H substitution at position 22 of the luxA subunit (SEQ ID NO:2), (f) a N to Y substitution at position 166 of the luxA subunit (SEQ ID NO:2), (g) a C to W substitution at position 170 of the luxA subunit (SEQ ID NO:2), or (h) a C to K substitution at position 170 of the luxA subunit (SEQ ID NO:2). In some embodiments, the luciferase having improved activity has at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to SEQ ID NOs:2, and comprises: (a) a P to R substitution at position 168, and an I to T substitution at position 309 of the luxA subunit (SEQ ID NO:2), (b) an I to V substitution at position 218, and a C to R substitution at position 224 of the luxA subunit (SEQ ID NO:2), (c) a T to I substitution at position 172, and a Q to R substitution at position 236 of the luxA subunit (SEQ ID NO:2), (d) a N to D substitution at position 286, and an E to D substitution at position 308 of the luxA subunit (SEQ ID NO:2), (e) a Q to L substitution at position 11, and an N to D substitution at position 261 of the luxA subunit (SEQ ID NO:2), or (f) an N to I substitution at position 130, and an E to G substitution at position 334 of the luxA subunit (SEQ ID NO:2).

In some embodiments, the improved luciferases can include vectors each containing one or more mutant or modified luciferase. For example, constructs can include vectors each containing one of the mutant or modified bacterial luciferases (e.g., having one or more mutations/modifications in SEQ ID NO:1). Constructs can be used, for example, as control template nucleic acid molecules. Vectors suitable for use are commercially available and/or produced by recombinant nucleic acid technology methods routine in the art. Nucleic acid molecules can be obtained, for example, by chemical synthesis, direct cloning from target region, or by nucleic acid amplification.

Constructs suitable for use in the methods typically include sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing the nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Articles of Manufacture/Kits

Embodiments of the present disclosure further provide for articles of manufacture or kits to the modified/mutant bacterial luciferases. An article of manufacture can include the modified/mutant bacterial luciferase, together with suitable packaging materials. In addition, the kits may also include suitably packaged reagents and materials needed for DNA immobilization, hybridization, detection, quantitation, such as solid supports, buffers, enzymes, and DNA standards.

Articles of manufacture can also contain a package insert or package label having instructions thereon for using the modified/mutant bacterial luciferases. Articles of manufacture may additionally include reagents for carrying out the methods disclosed herein (e.g., luciferin, or other appropriate substrate for modified/mutant bacterial luciferases). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example 1: Luciferase Mutation Screening

Bacterial luciferase (luxAB) from *A. fischeri* is often used in reporter systems, because of its low signal-to-noise, good expression, and simplicity of detection. This project was a directed evolution project to find luxAB variants with improved luminescent signal generation. Microbes with improved light generation would improve overall sensitivity in assays employing luxAB in reporter systems.

Bacterial luxAB-encoded luciferase is commonly used as a luminescent reporter in a variety of microorganisms. Luciferase catalyzes the reaction of molecular oxygen, reduced Flavin mononucleotide ($FMNH_2$), and a long-chain aldehyde, yielding the corresponding carboxylic acid, Flavin mononucleotide (FMN), water, and light (490 nm). The enzyme is a heterodimer consisting two homologous subunits, designated as the α- and β-subunits. The catalytic and substrate-binding sites are located in the α-subunit, whereas the β-subunit is required for maintaining the active conformation of the α-subunit. The diversification strategy for directed evolution of luxAB was focused on randomly mutating luxA (~300 amino acids) by error-prone polymerase chain reaction (PCR). The goal was to generate a library with 2-3 mutations per clone. Mutagenic cassettes were sub-cloned into an expression vector with T5 inducible promoter under Lac control, then transformed into BL21 *E. coli* expression strain to obtain a library of at least $10^4$ unique transformants. Mutagenic libraries were then arrayed, expressed, and screened in 96-well formats by luminescent activity assay on a microplate reader. A suitable library was generated, expression conditions were optimized, and a luminescent activity assay for primary screening was developed. Over 3,000 clones were expressed and assayed for in vivo luminescence activity. One library (Library 2.75) (~2 mutations/clone) was arrayed in 96-well culture plates and used to inoculate expression cultures and assay plates. A handful of clones emerged from the screen with either higher max RLU signal (Flash Kinetics) or slower RLU decay kinetics (Glow Kinetics), as compared to internal wild type luxAB controls. Table 1, below, depicts the top candidate list from the luxA gene mutagenic library screened for improved luminescence signal generation.

TABLE 1

| Plate | Position | Kinetic | Mutation 1 | Mutation 2 | Max RLU* |
|---|---|---|---|---|---|
| 1652 | H03 | glow | C170R | | 7.22 |
| 1653 | C05 | flash | P168R | I309T | 2.45 |
| 1634 | H08 | flash/glow | I218V | C224R | 2.13 |
| 1653 | H03 | glow | T172I | Q236R | 2.13 |
| 1631 | D11 | flash | N102K | | 2.10 |
| 1642 | H09 | flash | N286D | E308D | 1.97 |
| 1636 | G04 | flash | N264D | | 1.90 |
| 1635 | F07 | flash | N286D | | 1.83 |
| 1624 | D02 | flash | D22H | | 1.71 |
| 1621 | E10 | flash | Q11L | N261D | 1.46 |
| 1624 | A04 | glow | N130I | C224R | 1.33 |
| 1648 | H09 | flash | N166Y | | 1.23 |

All candidate clones were sequenced and re-assayed to confirm activity. In particular, clone 1652 H03 (with a C170R mutation) exhibited a 4-fold higher luminescence signal over wild type controls, with slow RLU decay kinetics (Glow), as shown in FIG. 1.

Example 2: Amino Acid Randomization at luxA Position 170

Random mutagenesis and screening of a random luxA library yielded a high RLU C170R mutant (i.e., clone 1652-H03). To determine if there was a better amino acid substitute than arginine at position 170, an NNK library at position 170 was constructed and arrayed into three 96-well culture storage plates containing wild type positive controls. All culture plates were expressed and assayed for luminescence activity.

Figure 2:
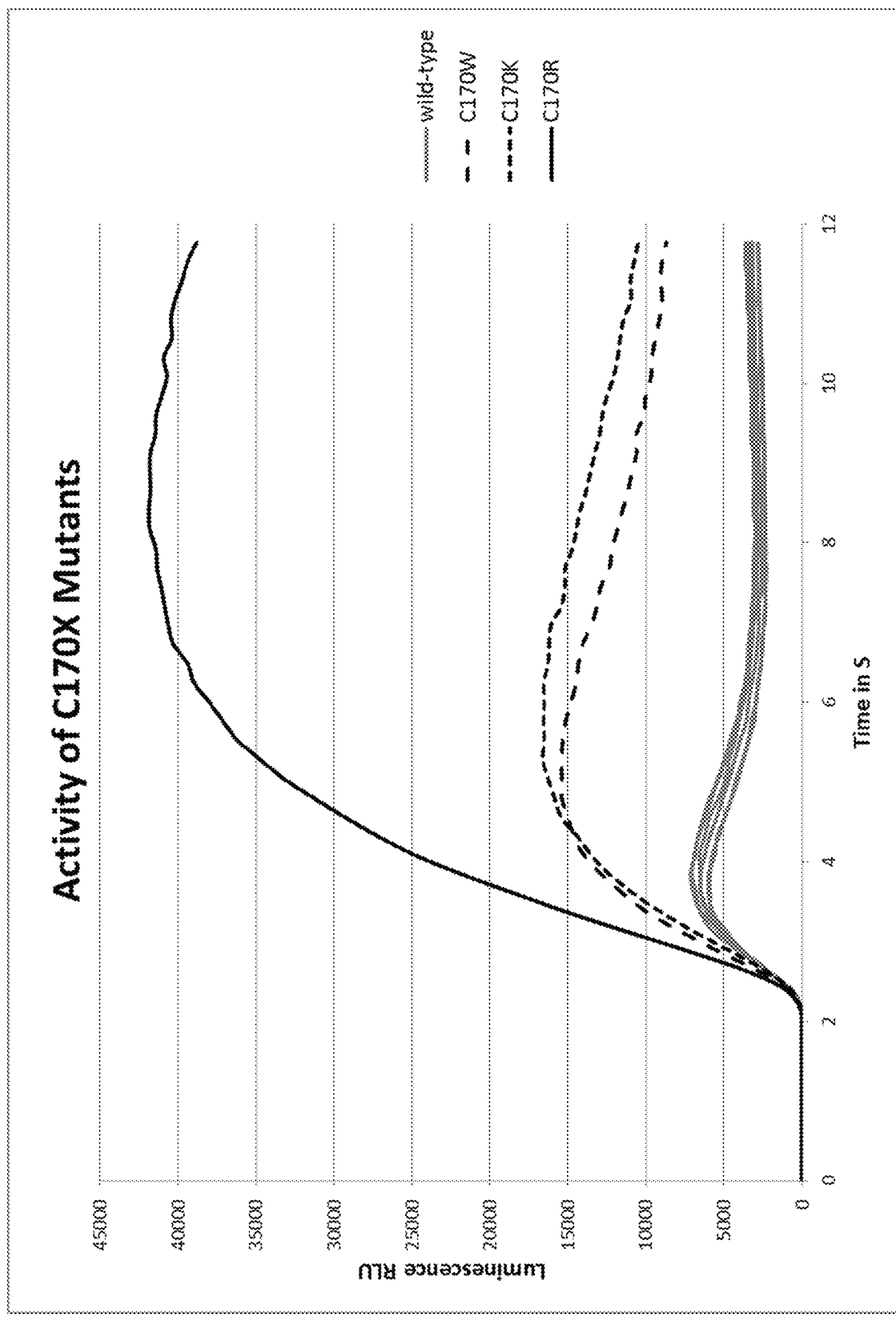
FIG. 2 shows the luminescence activity of the top luxA C170X mutant bacterial luciferase, as compared to wild type bacterial luciferase.

Library culture plates were used to inoculate Deep Well expression plates. Expression plates were incubated at 28° C. for 24 hours, in order to achieve uniform cell growth and protein expression. The expression culture was diluted ~80-fold in 1×LB media, and assayed to measure luminescence activity of the C170X library and compared to wild type internal controls. Subsequent sequencing of the 240 clones revealed that 16 of the possible 20 amino acid substitutions were present in the library. Assaying the library revealed that arginine substitution at position 170 actually resulted in the largest increase in activity over wild type (i.e., cysteine). Results also revealed that the next best substitutions at position 170 were Lysine (K) and Tryptophan (W), both increasing activity ~2.5-fold over wild type, as shown in FIG. 2. FIG. 2 shows the luminescence activity of top luxA C170X mutants. Arginine substitution at luxA amino acid position 170 results in approximately 7-fold increase of luminescence signal, and Tryptophan or Lysine substitutions result in approximately 2.5-fold increase in luminescent signal.

Example 3: luxAB Gel Quantification

Figure 3:
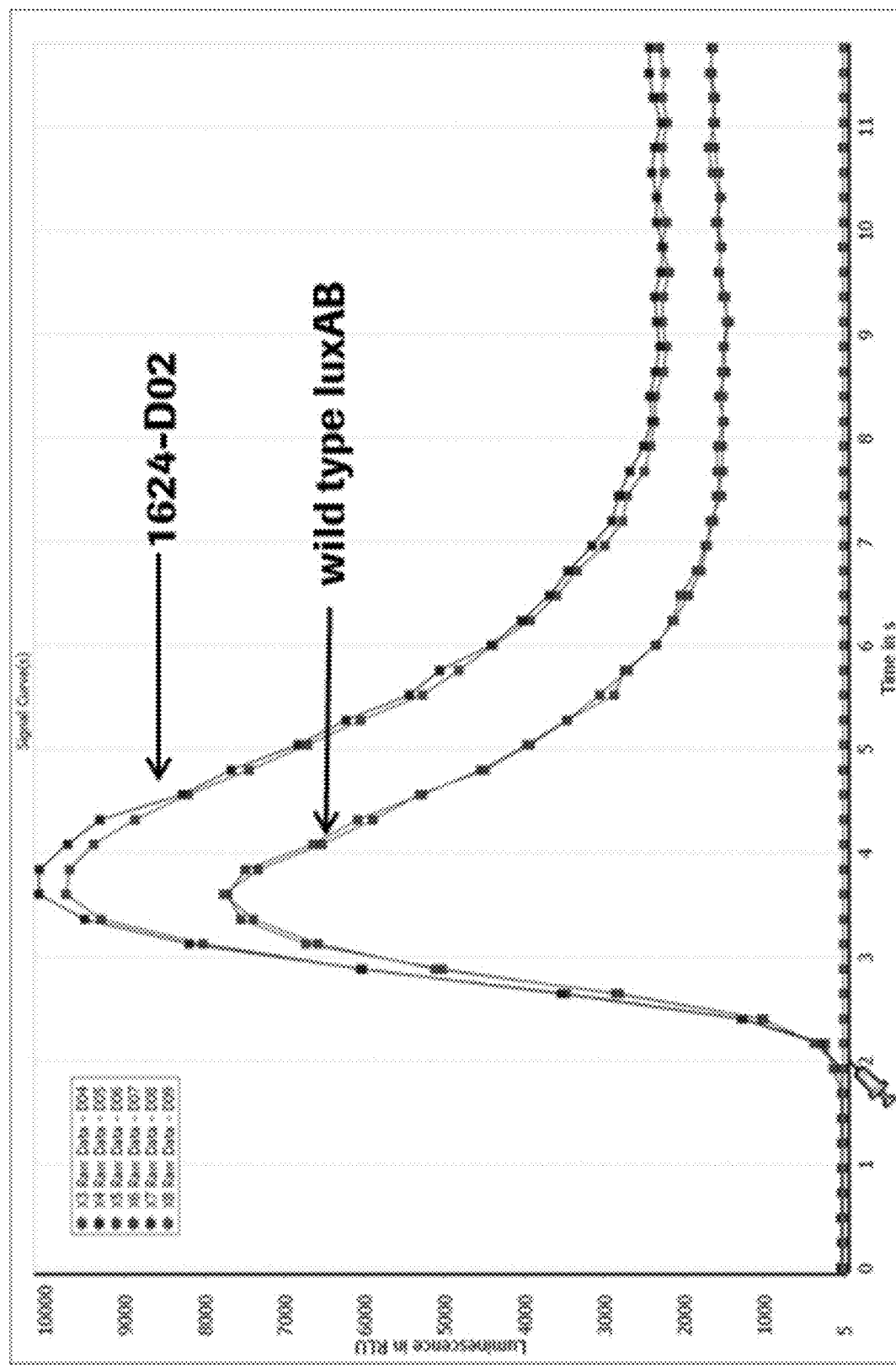
FIG. 3 shows the luminescence activity of the candidate modified bacterial luciferase clone 1624-D02 (with a D22H mutation), as compared to wild type bacterial luciferase.
Figure 4A:
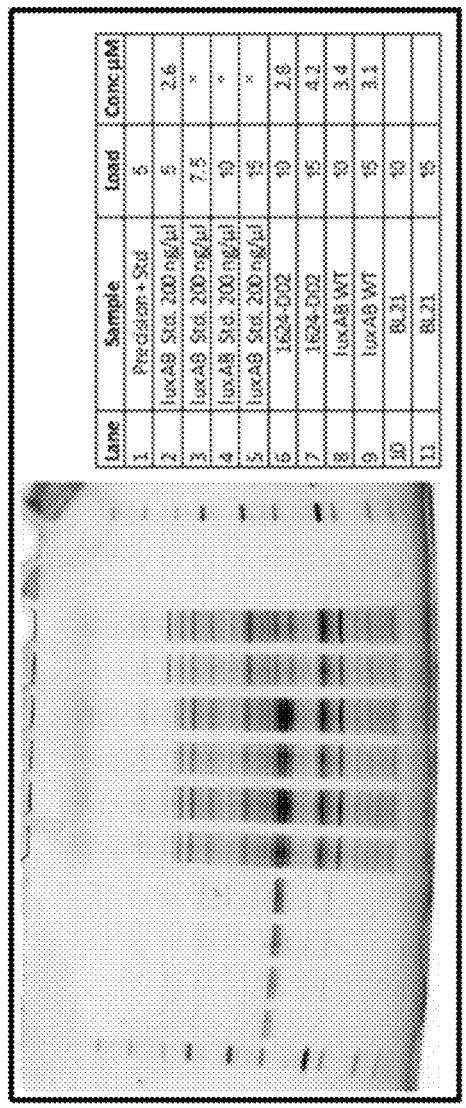
FIGS. 4A and 4B show the quantification of luxAB from expression cultures. In particular.
Figure 4B:
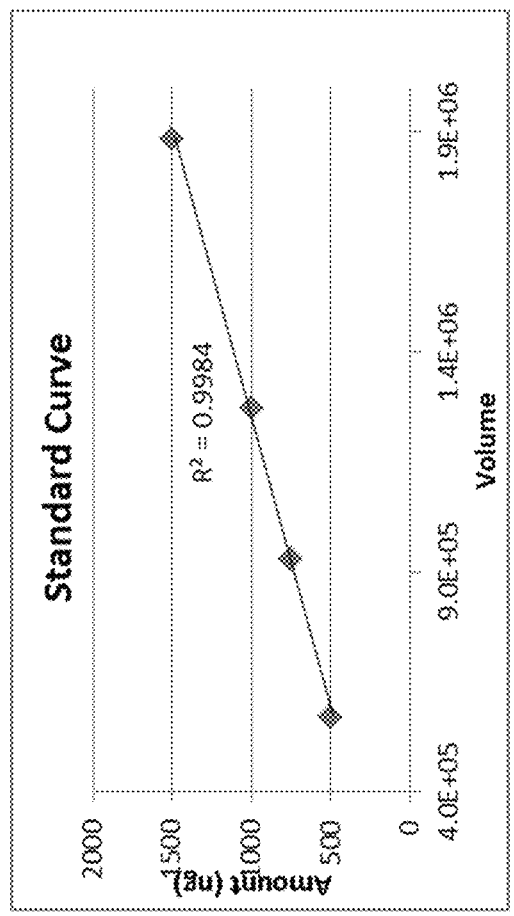

A method for quantifying luxAB from expression cultures was developed, in order to determine if luminescent activity differences were caused by expression or by kinetics of luminescent generating reaction. Flask cultures of clone 1624-D02, which exhibited a higher max RLU, and wild type luxAB were grown overnight in auto-induction media. Cultures were measured for activity, where clone 1624-D02 showed approximately 20% higher max RLU than did wild type, as shown in FIG. 3. Both cultures were then harvested by centrifugation, re-suspended, and lysed by sonication. Crude lysates were loaded onto stain-free polyacrylamide gel alongside purified *A. fischeri* luxAB (Roche Ref. #10-476-498-001). Distinct bands corresponding to both α- and β-subunits were visible in the crude lysate at several different load volumes, as shown in FIG. 4A. Additionally, quantification by normalizing to the purified luxAB standard curve showed that clone 1624-D02 was not overexpressed compared to wild type luxAB, as shown in FIG. 4A (lanes 8-9). *E. coli* BL21 cells without luxAB expression plasmid were run as negative controls. As expected, neither luxA, nor luxB were detected in BL21 crude lysates, as shown in FIG. 4A (lanes 10-11). FIG. 4B shows the standard curve.

Example 4: Other luxA Single Mutants

Figure 5:
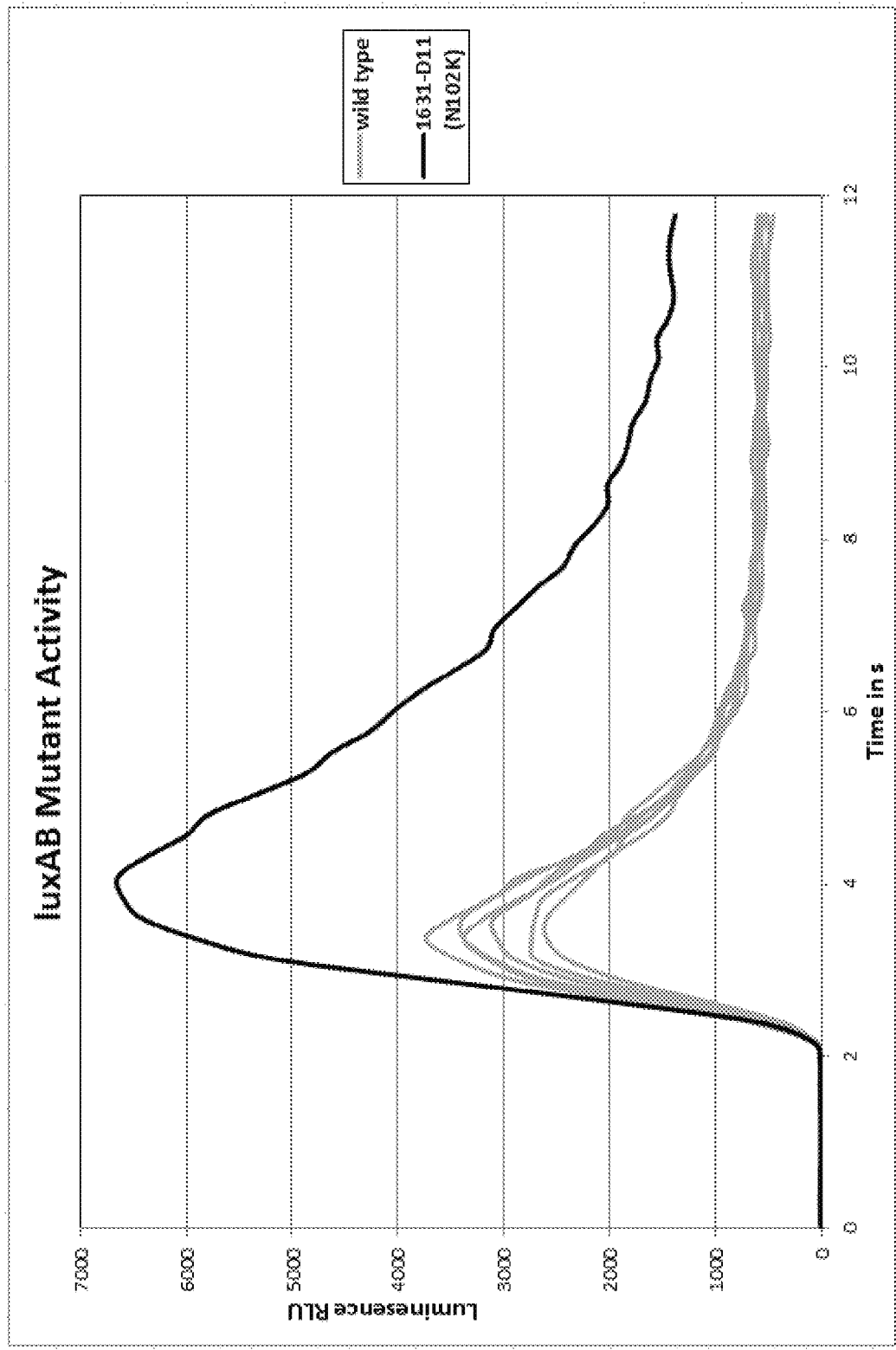
FIG. 5 shows the luminescence activity of the candidate modified bacterial luciferase clone 1631-D11 (with a N102K mutation), as compared to wild type bacterial luciferase.
Figure 6:
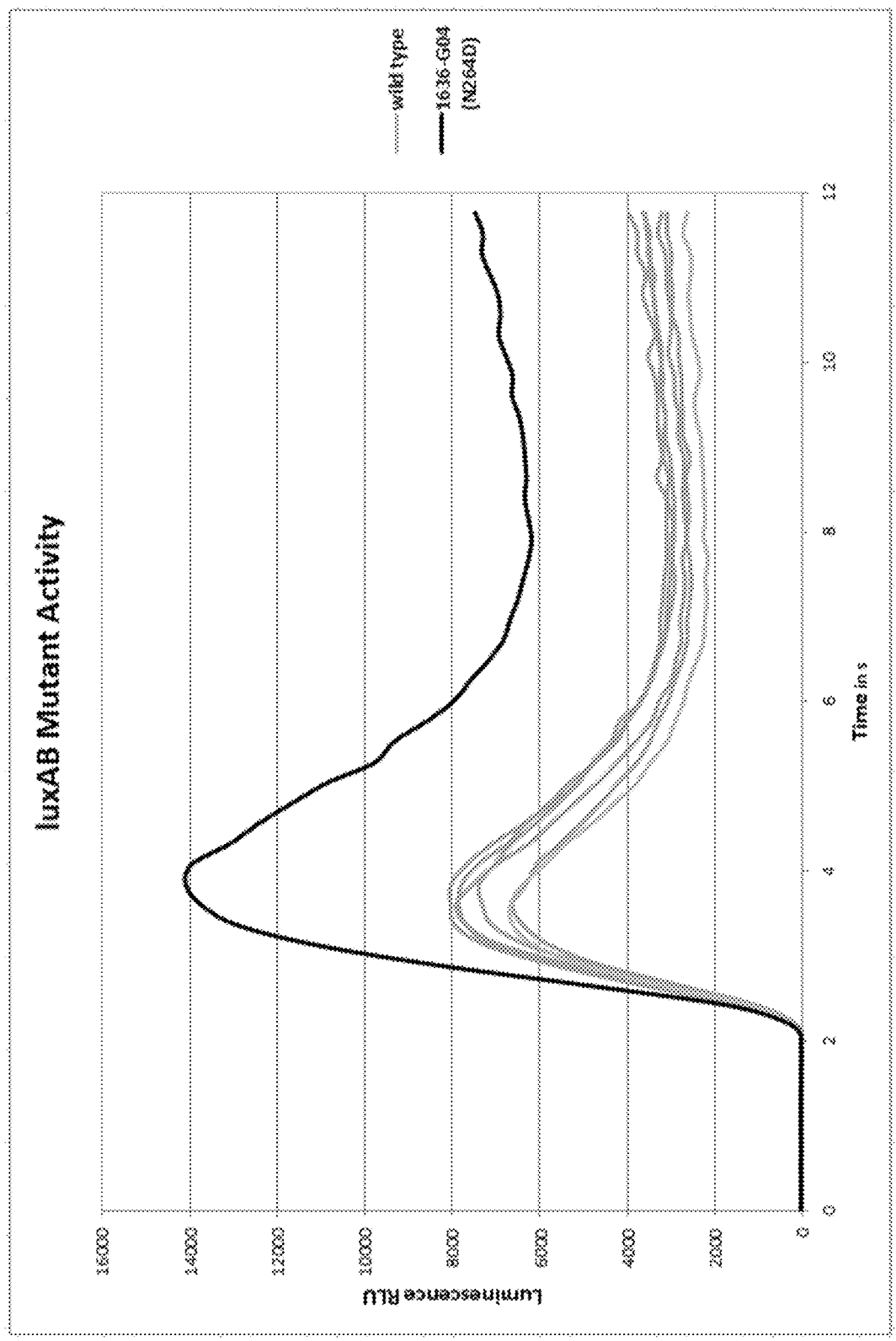
FIG. 6 shows the luminescence activity of the candidate modified bacterial luciferase clone 1636-G04 (with a N264D mutation), as compared to wild type bacterial luciferase.
Figure 7:
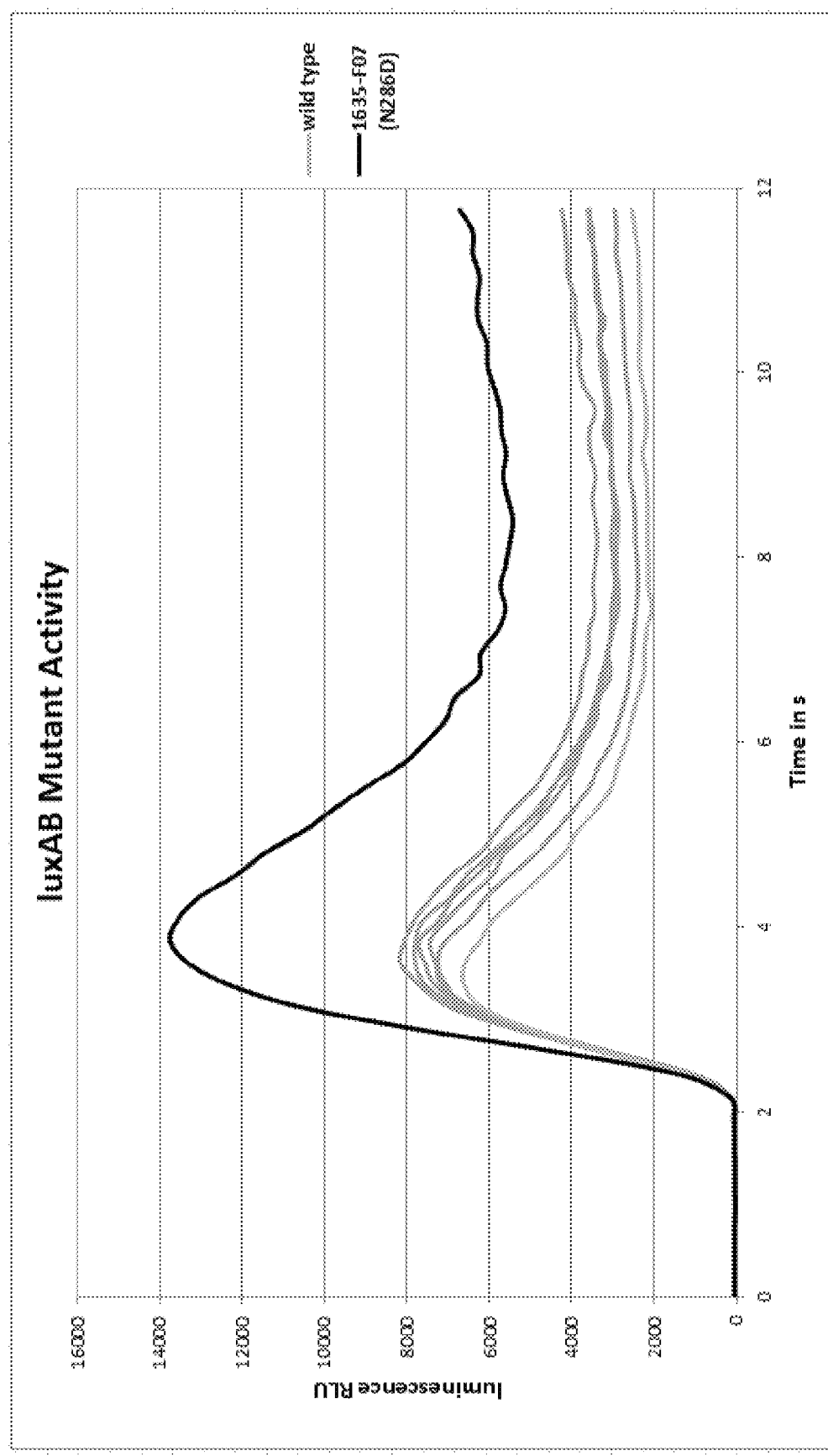
FIG. 7 shows the luminescence activity of the candidate modified bacterial luciferase clone 1635-F07 (with a N286D mutation), as compared to wild type bacterial luciferase.

Additional luxA single mutants were generated as described previously, and were also tested for their ability to generate a luminescent signal, as compared to wild type. In particular, mutants with a N102K mutation (labeled "1631-D11"), with a N264D mutation (labeled "1636-G04"), or with a N286D mutation (labeled "1635-F07") were generated and tested. Luminscence was tested as discussed previously. FIG. 5 shows the luminescence activity of the N102K mutant (labeled "1631-D11"), FIG. 6 shows the luminescence activity of the N264D mutant (labeled "1636-G04"), and FIG. 7 shows the luminescence activity of the N286D mutant (labeled "1635-F07"). Each of these single luxA mutants show improved luminescence as compared to wild type (see, FIGS. 5-7).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A modified bacterial luciferase having improved activity as compared to a control bacterial luciferase, wherein the improved activity is an increase in light production and/or slower signal decay, wherein the LuxA subunit of the modified bacterial luciferase comprises an amino acid sequence that is at least 99% identical to the LuxA subunit of the control bacterial luciferase, wherein the LuxA subunit of the control bacterial luciferase has the amino acid sequence of SEQ ID NO:2, wherein:
   (a) the amino acid of the modified bacterial luciferase corresponding to position 170 of SEQ ID NO:2 is R, W, or K;
   (b) the amino acid of the modified bacterial luciferase corresponding to position 102 of SEQ ID NO:2 is K;
   (c) the amino acid of the modified bacterial luciferase corresponding to position 22 of SEQ ID NO:2 is H; or
   (d) the amino acid of the modified bacterial luciferase corresponding to position 166 of SEQ ID NO:2 is Y.

2. The modified bacterial luciferase of claim 1, wherein the amino acid of the modified bacterial luciferase corresponding to position 170 of SEQ ID NO:2 is R.

3. A modified bacterial luciferase having improved activity as compared to a control bacterial luciferase, wherein the improved activity is an increase in light production and/or slower signal decay, wherein the LuxA subunit of the modified bacterial luciferase comprises an amino acid sequence that is at least 99% identical to the LuxA subunit of the control bacterial luciferase, wherein the LuxA subunit of the control bacterial luciferase has the amino acid sequence of SEQ ID NO:2, and comprises at least one amino acid substitution at position corresponding to position 11, 22, 102, 130, 166, 168, 170, 172, 218, 224, 236, 261, 264, 286, 308, or 309 of SEQ ID NO:2.

4. The modified bacterial luciferase of claim 3, wherein:
   (a) the amino acid of the modified bacterial luciferase corresponding to position 170 of SEQ ID NO:2 is R, W or K;
   (b) the amino acid of the modified bacterial luciferase corresponding to position 168 of SEQ ID NO:2 is R and corresponding to position 309 of SEQ ID NO:2 is T;
   (c) the amino acid of the modified bacterial luciferase corresponding to position 218 of SEQ ID NO:2 is V and corresponding to position 224 of SEQ ID NO:2 is R;
   (d) the amino acid of the modified bacterial luciferase corresponding to position 172 of SEQ ID NO:2 is I and corresponding to position 236 of SEQ ID NO:2 is R;
   (e) the amino acid of the modified bacterial luciferase corresponding to position 11 of SEQ ID NO:2 is L and corresponding to position 261 of SEQ ID NO:2 is D; or
   (f) the amino acid of the modified bacterial luciferase corresponding to position 130 of SEQ ID NO:2 is I and corresponding to position 224 of SEQ ID NO:2 is R.

5. The modified bacterial luciferase of claim 4, wherein the amino acid of the modified bacterial luciferase corresponding to position 170 of SEQ ID NO:2 is W or K.

* * * * *